United States Patent [19]

Sakurai et al.

[11] Patent Number: 4,845,102
[45] Date of Patent: Jul. 4, 1989

[54] THERAPEUTIC AGENT FOR THE TREATMENT OF PEPTIC ULCER DISEASE

[75] Inventors: Masao Sakurai, Saitama; Masayoshi Goto, Tokyo; Toshizo Tanaka, Saitama, all of Japan

[73] Assignee: Hoechst Japan Limited, Tokyo, Japan

[21] Appl. No.: 103,816

[22] Filed: Oct. 2, 1987

[30] Foreign Application Priority Data

Oct. 6, 1986 [JP] Japan .................. 61-236078

[51] Int. Cl.$^4$ .......................... C07D 473/04
[52] U.S. Cl. ........................ 514/263; 544/271; 544/273
[58] Field of Search .............. 544/271, 273; 514/263

[56] References Cited

U.S. PATENT DOCUMENTS

| 4,242,345 | 12/1980 | Brenner et al. | 544/271 |
| 4,289,776 | 8/1981 | Mohler et al. | 514/263 |
| 4,291,037 | 9/1981 | Brenner et al. | 514/263 |
| 4,511,557 | 4/1985 | Gauri | 514/263 |
| 4,544,556 | 10/1985 | Fedi et al. | 544/273 |
| 4,636,507 | 1/1987 | Kreutzer et al. | 514/263 |

FOREIGN PATENT DOCUMENTS 1075690 4/1980 Canada .

OTHER PUBLICATIONS

Ter. Ark, vol. 57, pp. 52–55, (1985).

Primary Examiner—Paul Lieberman
Assistant Examiner—Helene Kirschner
Attorney, Agent, or Firm—Finnegan, Henderson, Farabow, Garrett and Dunner

[57] ABSTRACT

Therapeutic agent for the treatment of peptic ulcer disease comprising as active ingredient at least one compound of formula I

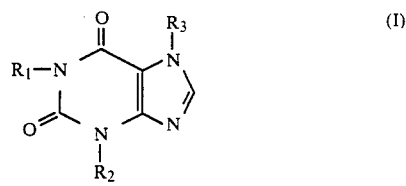

wherein
$R_1$ = 5-oxohexyl,
$R_2$ = methyl or
$R_3$ = $C_2$–$C_4$-alkyl or one compound of formula I,
wherein
$R_1$ = 4-oxopentyl,
$R_2$ = methyl or ethyl, and
$R_3$ = $C_2$–$C_4$ alkyl,
is disclosed, together with a process for using the agent.

8 Claims, No Drawings

THERAPEUTIC AGENT FOR THE TREATMENT OF PEPTIC ULCER DISEASE

This invention relates to pharmaceuticals suitable for use in the treatment of peptic ulcer disease. Peptic ulcer is an ulceration of the mucous membrane of the stomach and/or duodenum; the mucous membrane is damaged by the action of hydrochloric acid and pepsin due to its decreased resistance to the aggressive factors induced by various causes including physical and physiological stress.

Until recently, sodium bicarbonate and aluminum compounds had been used to neutralize gastric acid as aggressive factor. The drugs commonly used now to treat peptic ulcer disease include anticholinergics, gastroprotective agents, drugs improving mucosal blood flow, and $H_2$-receptor antagonists.

Drugs for peptic ulcers are administered for along period of time and are required to have the fewest adverse effects as well as high efficacy. However, the available drugs are not necessarily satisfactory in safety and efficacy. In addition there is another problem associated with the use of the drugs, namely the relapse of ulcer after drug treatment is stopped. For example, the $H_2$-receptor antagonists are very effective in improving gastric and duodenal ulcers by inhibiting gastric acid secretion but ulcers recur at high incidence after discontinued treatment with the drugs.

As a result of our extensive studies for superior therapeutics for peptic ulcer disease, we have found that 1,2,3,6-tetrahydro-3-methyl-1-(5-oxohexyl)-7-propyl-purine-2,6-dione (recommended International Nonproprietary Name: propentofylline) and related compounds have high efficacy and safety enough to be new drugs suitable for use in the treatment of the disease.

The present invention provides a therapeutic agent for the treatment of peptic ulcer disease containing, as active ingredient, at least one compound of the general formula I

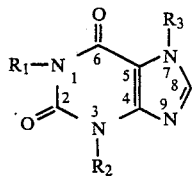

wherein $R_1$ is 4-oxopentyl or 5-oxohexyl, $R_2$ is methyl or ethyl, and $R_3$ is $C_2-C_4$-alkyl.

Propentofylline of the above general formula wherein $R_1$ is 5-oxohexyl, $R_2$ is methyl, and $R_3$ is propyl is a xanthine derivative which has been shown to dilate cerebral blood vessels, improve cerebral energy metabolism, red blood cell deformability, and cerebral edema, and decrease blood viscosity (c.f. for example, U.S. Pat. No. 4,289,776). We have found that in addition to the above pharmacological effects propentofylline and related compounds have improving effects on gastric ulcer. Pentoxifylline, substituted by methyl at the 7-position in propentofylline, has already been reported by Vorobyev and Samsonov to have antiulcer effects (Ter. Ark. 57, 52-55, 1985). HOwever, the efficacy is not high enough to be a promising drug for peptic ulcer disease. The compounds of this invention have been shown, as described below, to be much more effective than pentoxyifylline and to have low toxicity, indicating that they are effective antiulcer drugs producing a low incidence of side effects.

Possible administration routes of the compounds of this invention are oral, intravenous, subcutaneous, intramuscular, and rectal. The clincial dose is about 300–900 mg/60 kg body weight, preferably about 150–600 mg/60 k body weight. Usable dsage forms are tablets, sugar-coated tablets, pills, capsules, powders, granules, suppositories, and injections. The tablets, sugar-coated tablets, capsules, and granules are desirable for oral, the injections for parenteral, and the suppositories for rectal administration.

The compounds of this invention can be used each as a monopharmacon or as a combination or in combination with other agents for the treatment of peptic ulcer disease including antacids.

For injection, the powder for injection is usable. In this case, the compounds of this invention are dissolved in water containing one or more adequate water-soluble excipients such as mannitol, sucrose, lactose, maltose, glucose, and fructose. Then the solution is put into the vial or ampule, which is sealed after lyophilization of the contents.

For oral administration, an enteric-coated preparation is possible in addition to the dosage forms listed above. In this case, the tablets, granules, or fine granules are prepared using the following as additives as required: excipients such as mannitol, sucrose, lactose, maltose, starch, silica, and calium phosphate; lubricants such as talc and magnesium stearate; binders such as sodium arabic; and disintegrating aids such as calcium carboxymethylcellulose. Then, the tablets, granules, or fine granules are coated with one or more enteric bases with, if required, a coloring agent such as titanium dioxide. The bases for enteric coating include cellulose acetate phthalate, hydroxypropylmethylcellulose phthalate, hydroxypropylmethylcellulose acetylsuccinate, polyvinyl alcohol phthalate, styrene-maleic anhydride copolymers, styrene-maleic acid copolymers, methyl methacrylate-methacrylic acid copolymers, and methyl acrylate-methacrylic acid copolymers. The enteric-coated granules or fine granules are preferably filled into capsules.

Enteric-coated capsules can be obtained by coating capsules manufatured by a conventinal method with one or more of the enteric bases listed above or by manufacturing capsules with an enteric base alone or in admixture with gelatin.

Suppositories can be prepared as follows. The compounds of this invention are mixed homogenously with (a) a lipophilic base such as cacao butter or adeps solidus in various proportions or (b) a hydrophilic base such as polyethylene glycol or glycerol. The mixture containing the compounds of this invention is put into molds.

The weight ratio of the active ingredient(s) of the formula I and the respective carrier or excipient can vary within a very wide range; preferably it is within the range of about 1:100 to about 100:1.

The antiulcer effects and the toxicological profile of the compounds of this invention were as follows. The compounds tested are shown in Table 1. Pentoxifylline=1,2,3,6-tetrahydro-3,7-dimethyl-1-(5-oxohexyl)-purine-2,6-dione was used as a reference drug for the pharmacological studies.

TABLE 1

| Compound No. | Compounds of this invention | | |
|---|---|---|---|
| | $R_1$ | $R_2$ | $R_3$ |
| 1 | $CH_3-\underset{\underset{O}{\|\|}}{C}-(CH_2)_4-$ | $-CH_3$ | $-C_2H_5$ |
| 2* | $CH_3-\underset{\underset{O}{\|\|}}{C}-(CH_2)_4-$ | $-CH_3$ | $-(CH_2)_2-CH_3$ |
| 3 | $CH_3-\underset{\underset{O}{\|\|}}{C}-(CH_2)_3-$ | $-CH_3$ | $-(CH_2)_2-CH_3$ |
| Pentoxifylline (Reference) | $CH_3-\underset{\underset{O}{\|\|}}{C}-(CH_2)_4-$ | $-CH_3$ | $-CH_3$ |

*Propentofylline

1. Antiulcer effects 1.1 Protective efrrect on gastric ulcer induced by restraint plus water-immersion stress in rats Male Sprague-Dawley rats weighing 250-300 g wer eused in groups of 5-24. The animals were given the compounds by the oral route after fastin overnight. Immediately, under light ether anesthesia they were placed in a restraint box and immersed in water at 20° C. for 6 to 7 hours. Then the animals were sacrificed, and their stomachs were isolated, inflated with 4 ml of 1 % formalin for 10 minutes, opened along the greater cruvature, and examined for the rpesence of agstric erosions. The longest axis of each erosion induced on the glandular section of the stomach was measured, and the sum of the lengths was defined as an ulcer index. The results are shown in Tables 2 and 3.

TABLE 2

Protective effect on stress-induced gastric ulcer in rats (Dose dependency)

| Compound | Dose (mg/kg, po) | No. of animals | Ulcer index (mm) | Inhibition (%) |
|---|---|---|---|---|
| Control (Distilled water) | 0 | 12 | 37.3 ± 5.1 | — |
| Compound 2 (= propentofylline) | 5 | 6 | 22.6 ± 9.8 | 39.4 |
| | 10 | 6 | 13.3 ± 5.4* | 64.3 |
| | 25 | 6 | 9.1 ± 3.1* | 75.6 |
| Control (Distilled water) | 0 | 10 | 32.9 ± 5.9 | — |
| Pentoxifylline | 10 | 10 | 24.4 ± 4.0 | 25.8 |
| | 25 | 10 | 15.8 ± 4.1* | 52.0 |
| | 50 | 8 | 5.3 ± 1.2** | 83.9 |

**$P < 0.01$,
*$P < 0.05$ (P = significance)
Each value represents the mean ± S.E. (Standard Error)

TABLE 3

Protective effect on stress-induced gastric ulcer in rats (Efficacy comparison)

| Compound | Dose (mg/kg, po) | No. of animals | Ulcer index (mm) | Inhibition (%) |
|---|---|---|---|---|
| Control (Distilled water) | 0 | 24 | 19.7 ± 2.9 | — |
| Compound | | | | |
| 1 | 10 | 5 | 4.5 ± 0.9** | 77.2 |
| 2 | 10 | 5 | 8.6 ± 2.3* | 56.3 |
| 3 | 10 | 5 | 6.5 ± 1.6** | 67.0 |
| Pentoxifylline | 10 | 5 | 17.2 ± 5.6 | 12.7 |

**$P < 0.01$,
*$P < 0.05$
Each value represents the mean ± S.E.

1.2 Protective effect on ethanol-induced gastric ulcer in rats

Male Sprague-Dawley rats weighing 250-300 g were used in groups of 5-21. After fasting overnight, the animals were given orally the compounds. Thirty minutes later they received absolute ethanol (1 ml/body) orally and were sacrificed after 60 minutes. The stomach was removed and examined for erosions. The ulcer index was obtained in the same way as under 1.1. The results are shown in Table 4 and 5.

TABLE 4

Protective effect on ethanol-induced gastric ulcer in rats (Dose dependency)

| Compound | Dose (mg/kg, po) | No. of animals | Ulcer index (mm) | Inhibition (%) |
|---|---|---|---|---|
| Control (Distilled water) | 0 | 14 | 132.5 ± 12.3 | — |
| Compound 2 | 10 | 10 | 51.0 ± 13.2** | 61.5 |
| | 25 | 10 | 32.6 ± 9.1** | 75.4 |
| | 50 | 8 | 13.6 ± 9.3** | 89.7 |
| Pentoxifylline | 10 | 10 | 65.8 ± 12.1** | 50.3 |
| | 25 | 10 | 47.8 ± 15.3 | 63.9 |
| | 50 | 10 | 18.7 ± 6.2** | 85.9 |

**$P < 0.01$
Each value represents the mean ± S.E.

TABLE 5

Protective effect on ethanol-induced gastric ulcer in rats (Efficacy comparison)

| Compound | Dose (mg/kg, po) | No. of animals | Ulcer index (mm) | Inhibition (%) |
|---|---|---|---|---|
| Control (Distilled water) | 0 | 21 | 164.7 ± 19.4 | — |
| Compound | | | | |
| 1 | 10 | 5 | 25.3 ± 10.9** | 84.6 |
| 2 | 10 | 5 | 21.6 ± 4.6** | 86.9 |
| Pentoxifylline | 10 | 5 | 34.9 ± 10.9** | 78.8 |

**$P < 0.01$
Each value represents the mean ± S.E.

1.3 Inhibitory effect on gastric hemorrhage in rats

The method of Maeda-Hagiwara and Watanabe (Eur. J. Pharmacol. 89, 243-250, 1983) was used. Male Sprague-Dawley rats weighing 250-300 g were employed in groups of 10-14. After 24 hours fasting, the pylorus was ligated under light ether anesthesia. Then, 200 mg/kg of 2-deoxy-D-glucose was administered intravenously in combination with 40 mg/kg of indomethacin suspended in 0.5 % carboxymethylcellulose by the subcutaneous route. After 1 hour the test compounds were injected intraperitoneally. Two hours later, the animals were exsanguinated under ether anesthesia and their stomachs were isolated. Gastric juice was collected and filtered. The amount of discharged blood was expressed as that of hemoglobin in mg per rat. The results are given in Table 6.

TABLE 6

Inhibitory effect on gastric hemorrhage in rats

| Compound | Dose (mg/kg, i.p.) | No. of animals | Amount of hemoglobin (mg/rat) |
|---|---|---|---|
| Control (Physiological saline) | 0 | 14 | 26.0 ± 3.8 |
| Compound 2 | 12.5 | 10 | 27.0 ± 3.0 |
| | 25 | 10 | 14.4 ± 1.4* |
| | 50 | 10 | 12.5 ± 1.6** |
| Pentoxifylline | 25 | 10 | 19.6 ± 2.0 |
| | 50 | 10 | 17.3 ± 2.3 |

**$P < 0.01$,
*$P < 0.05$
Each value represents the mean ± S.E.

2. Toxicological profile $LD_{50}$ values of compound 2 for mice and rats were 900 and 1,150 mg/kg for oral dosing and 168 and 180 mg/kg for intravenous injection, respectively. Comparable $LD_{50}$ values for the compounds of this invention were found after intraperitoneal administration to mice with 250–500 mg/kg for compound 1, 296 mg/kg for compound 2, and 300–600 mg/kg for compound 3.

Compound 2 was administered orally to rats at 150 and 50 mg/kg/day for 3 months. This study included: observation of toxic signs during the treatment; macroscopic and microscopic examinations of main organs including the brain, heart, liver, kidney, bone marrow, adrenal, and lung; and biochemical tests of the blood and urine. There were no abnormalities at either level of treatment except that slight salivation occurred at 150 mg/kg/day.

Examples of the invention will be as follows.

EXAMPLE 1

An injectable preparation was prepared as follows. Compound 2 (20 g) and sodium chloride (16 g) were added to distilled water for injection to make 2,000 ml. The solution was filtered through a 0.22 μm Millipore filter and divided at 5 ml into 5 ml ampules, which were sealed and sterilzied in an autoclave.

EXAMPLE 2

Tablets each containing 115 mg of Compound 2 were prepared by a conventional method from a mixture of 500 g of Compound 2 with 250 g of lactose, 150 g of corn starch, 150 g of calcium carboxymethylcellulose, 42 g of talc, 5 g of magnesium stearate, and 3 g of silica. The tablets were coated with a suspension containing 500 ml of water, 40 g of hydroxypropylmethylcellulose, 2 g of polyethyleneglycol with the average molecular weight of 6000, 3.5 g of titanium dioxide and 3 g of talc.

Effects of the invention:

As revealed by our studies described above, the compounds of this invention were shown to possess potent antiulcer effects and low toxicity. For exmaple, Compound 2 was (a) approximately 2 to 3 times more effective than pentoxifylline in improving stress-induced gastric ulcers, and had (b) inhibitory effects on gastric hemorrhage while pentoxifylline did not have a statistically significant effect, and (c) low toxicity.

The results indicate that the compounds of this invention are potent therapeutics for peptic ulcer disease which possess an excellent tolerability and inhibit gastric hemorrhage in patients with peptic ulcers.

We claim:

1. A process for treating peptic ulcer disease comprising the step of administering a pharmaceutical composition that comprises a pharmaceutically acceptable carrier or excipient and a therapeutically effective amount of an agent that is represented by formula I

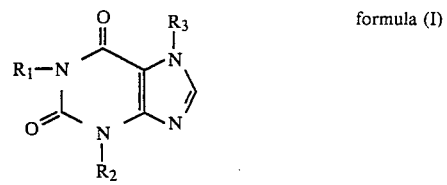

formula (I)

wherein
$R_1$ is 4-oxopentyl or 5-oxohexyl,
$R_2$ is methyl or ethyl, and
$R_3$ is $C_2$-$C_4$ alkyl.

2. A process as claimed in claim 1, wherein $R_1$ of formula I is 4-oxopentyl.

3. A process as claimed in claim 2, wherein $R_2$ of formula I is methyl.

4. A process as claimed in claim 3, wherein $R_3$ of formula I is propyl.

5. A process as claimed in claim 1, wherein $R_1$ of formula I is 5- oxohexyl.

6. A process as claimed in claim 5, wherein $R_2$ of formula I is methyl.

7. A process as claimed in claim 6, wherein $R_3$ of formula I is propyl.

8. A process as claimed in claim 6, wherein $R_3$ of formula I is ethyl.

* * * * *